(12) United States Patent
Feldhahn et al.

(10) Patent No.: US 10,369,309 B2
(45) Date of Patent: Aug. 6, 2019

(54) METHOD AND DEVICE FOR OPERATING BREATHING APPARATUS

(71) Applicant: WEINMANN GERAETE FUER MEDIZIN GMBH + CO. KG, Hamburg (DE)

(72) Inventors: Karl-Andreas Feldhahn, Hamburg (DE); Christof Schroeter, Karlsruhe (DE); Andreas Rensmann, Karlsruhe (DE); Uwe Strempel, Pforzheim (DE); Regina Schaefer, Iffezheim (DE); Matthias Schwaibold, Karlsruhe (DE)

(73) Assignee: Loewenstein Medical Technology S.A, Luxembourg (LU)

( * ) Notice: Subject to any disclaimer, the term of this patent is extended or adjusted under 35 U.S.C. 154(b) by 581 days.

(21) Appl. No.: 14/914,347

(22) PCT Filed: Aug. 29, 2014

(86) PCT No.: PCT/DE2014/000454
§ 371 (c)(1),
(2) Date: Feb. 25, 2016

(87) PCT Pub. No.: WO2015/027981
PCT Pub. Date: Mar. 5, 2015

(65) Prior Publication Data
US 2016/0202890 A1    Jul. 14, 2016

(30) Foreign Application Priority Data

Aug. 29, 2013 (DE) .......................... 10 2013 014 303
Mar. 28, 2014 (DE) .......................... 10 2014 004 448

(51) Int. Cl.
*G06F 3/048*  (2013.01)
*A61M 16/00*  (2006.01)
(Continued)

(52) U.S. Cl.
CPC .... *A61M 16/0051* (2013.01); *A61M 16/0057* (2013.01); *A61M 16/024* (2017.08); *A61M 16/109* (2014.02); *A61M 16/16* (2013.01); *G06F 3/02* (2013.01); *G06F 3/0412* (2013.01); *G06F 3/0482* (2013.01); *G06F 3/04842* (2013.01); *G06F 3/04847* (2013.01); *G06F 3/04883* (2013.01); *G06F 3/04886* (2013.01); *G16H 40/63* (2018.01);
(Continued)

(58) Field of Classification Search
CPC . A61M 16/0003; A61M 16/16; G06F 19/326; G06F 3/0488
See application file for complete search history.

(56) References Cited

U.S. PATENT DOCUMENTS 5,881,723 A * 3/1999 Wallace ............ A61M 16/0051
128/204.21
6,158,432 A  12/2000 Biondi et al.
(Continued)

*Primary Examiner* — Linh K Pham
(74) *Attorney, Agent, or Firm* — Abel Schillinger, LLP

(57) ABSTRACT

The invention relates to a device for operating a breathing apparatus with a touch-sensitive graphical display and just one other mechanical operating element, wherein the basic treatment can be started by pressing down the mechanical operating element, and additional adjustments are made using the touch-sensitive graphical display.

21 Claims, 15 Drawing Sheets

(51) Int. Cl.
   *G06F 3/02*      (2006.01)
   *G06F 3/041*     (2006.01)
   *G06F 3/0482*    (2013.01)
   *G06F 3/0484*    (2013.01)
   *G06F 3/0488*    (2013.01)
   *G16H 40/63*     (2018.01)
   *A61M 16/10*     (2006.01)
   *A61M 16/16*     (2006.01)

(52) U.S. Cl.
   CPC . *A61M 2205/14* (2013.01); *A61M 2205/3386* (2013.01); *A61M 2205/505* (2013.01); *A61M 2205/52* (2013.01); *A61M 2205/587* (2013.01); *A61M 2230/40* (2013.01)

(56) References Cited

U.S. PATENT DOCUMENTS

| | | |
|---|---|---|
| 2003/0062045 A1 | 4/2003 | Woodring et al. |
| 2004/0019259 A1* | 1/2004 | Brown .................. A61B 5/0002 |
| | | 600/300 |
| 2008/0072896 A1* | 3/2008 | Setzer ..................... G06F 19/00 |
| | | 128/200.24 |
| 2009/0107498 A1* | 4/2009 | Plattner ................ A61M 16/024 |
| | | 128/204.23 |
| 2010/0199102 A1* | 8/2010 | Knepper .............. A61M 16/024 |
| | | 713/189 |
| 2011/0138308 A1 | 6/2011 | Palmer et al. |
| 2011/0154241 A1 | 6/2011 | Skidmore et al. |
| 2011/0259332 A1* | 10/2011 | Sanchez .............. A61M 16/024 |
| | | 128/204.21 |
| 2011/0308518 A1* | 12/2011 | McGroary ........ A61M 16/0051 |
| | | 128/203.12 |
| 2012/0024286 A1* | 2/2012 | Boring .............. A61M 16/0051 |
| | | 128/204.21 |
| 2012/0192867 A1* | 8/2012 | Lewis ............... A61M 16/0051 |
| | | 128/204.21 |
| 2013/0254695 A1* | 9/2013 | Lambourne ........... G06F 3/0484 |
| | | 715/771 |
| 2015/0193585 A1* | 7/2015 | Sunna .................... G16H 40/63 |
| | | 345/173 |

* cited by examiner

METHOD AND DEVICE FOR OPERATING BREATHING APPARATUS

BACKGROUND OF THE INVENTION

Field of the Invention

The invention relates to an operating system for a breathing apparatus.

Discussion of Background Information

Breathing apparatuses usually have separate operating and information or display elements. Operating elements are in the form of switches or rotary knobs, for example. The adjustments made using the operating elements can then be read on separate displays. This results in complex operation for the user with menu guidance which is not very intuitive.

The object of the present invention is therefore to provide a user-friendly and intuitively operable operating system for a breathing apparatus. In particular, the user is supposed to be able to make important adjustments quickly without having to deeply navigate through nested menu structures.

The object is achieved by means of the features of the main claim.

SUMMARY OF THE INVENTION

Operating device for a breathing apparatus comprising: a touch-sensitive graphical display which at least occasionally represents the range of values for a breathing parameter and numerically displays at least individual values, a memory for breathing-parameter values, at least one data point associated with the range of values,
- at least one position on the touch-sensitive graphical display which is associated with the data point using switching logic,
- switching logic which, when the position on the touch-sensitive graphical display which is associated with the data point using switching logic is touched,
- causes at least one numerical value associated with the data point and/or a confirmation field for the numerical value to be displayed,
- switching logic which, when the numerical value or the confirmation field is touched, applies this numerical value to the associated respiratory gas parameter and writes this numerical value, with the associated respiratory gas parameter, to the memory.

Beside the touch-sensitive display, only one further operating element is provided according to the invention. This operating element can be mechanically operated and therefore differs from the touch surfaces on the display. According to the invention, the breathing apparatus is switched on and off via the operating element, with the result that a basic therapy appropriate for the patient can be activated using only one button. For this purpose, the operating element is connected to the blower motor using switching logic and activates this motor and the memory in order to retrieve and use stored therapy data such as pressure values. In addition, individual values such as pressure values can be adapted using the enter keys of the touch-sensitive display. However, operation using the enter keys of the touchscreen is not necessary to start the therapy according to the invention.

Operating device for a breathing apparatus having a touch-sensitive graphical display and only one further mechanical operating element, in which case the basic therapy can be started by pressing down the mechanical operating element and additional adjustments are made using the touch-sensitive graphical display.

The invention also provides for the finger position to already be detected when approaching the screen. The operating logic would then be similar to that described above, but touching of the screen would then already be the confirmation of the adjusted value, for example.

The operating device for a breathing apparatus, preferably for a CPAP, APAP, bi-level or home therapy breathing apparatus, is equipped with a display for displaying information and for displaying operating fields for the user and with at least one touch-sensitive input field.

BRIEF DESCRIPTION OF THE DRAWINGS

Exemplary embodiments of the invention are schematically illustrated in the drawings, in which.

DETAILED DESCRIPTION OF EMBODIMENTS

Figure 1:
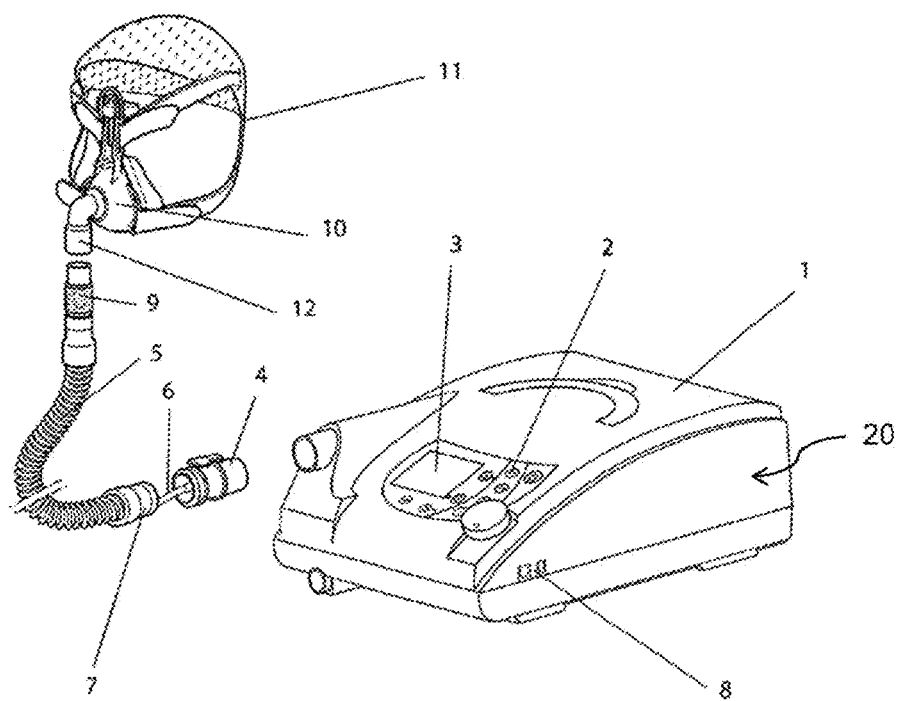
FIG. 1 shows a perspective illustration of a breathing apparatus with a breathing mask and a respiratory gas hose.

FIG. 1 shows the fundamental structure of a breathing device. An operating element (2) and an operating and information system (3) consisting of a display (13) and a touch-sensitive input unit (15) with at least one operating field (14) are arranged in the region of an apparatus housing (1) of the breathing apparatus (20) having a respiratory gas source in the interior of the apparatus. A connecting hose (5) is connected via a coupling (4). An additional pressure-measuring hose (6) which can be connected to the apparatus housing (1) via a pressure inlet connection piece (7) can run along the connecting hose (5). In order to make it possible to transmit data, the apparatus housing (1) has at least one interface (8). A humidifier (30) can also be adapted.

An exhalation element (9) is arranged in the region of an extent of the connecting hose (5) which faces away from the apparatus housing (1). An exhalation valve may likewise be used.

FIG. 1 also shows a patient interface which is in the form of a respiratory mask (10) and is implemented as a nasal mask. Fixing in the region of a patient's head can be carried out using a head cover (11). In the region of its extent facing the connecting hose (5), the patient interface (10) has a coupling element (12).

Data, for example dead space volume, can be input and/or output via the interface (8). The interfaces may be wired, in the form of an infrared interface, in the form of a Bluetooth interface or in the form of a USB. A card slot is preferably also provided. The interface (8) may also be in the form of a LAN interface or another interface for connection to the Internet. An oxygen connection valve can be adapted for the breathing device in the region of an apparatus housing. It is conceivable for the respiratory gas to additionally be enriched with oxygen in order to improve patient care.

Data which are extraneous to the therapy can also be loaded into the breathing apparatus according to the invention via the interface (8)—for example in the form of a card slot or USB—and can be executed by said apparatus. The idea is thus to display photos or videos, for example, in the region of the display by means of storage media via the interface (8). If external storage media are detected by the apparatus, the user must confirm an enquiry in the operating field, whereupon the data are either stored in the region of the breathing apparatus or are executed.

The breathing apparatus (20) according to the invention is designed in such a manner that it can be connected to a patient via a hose and a patient interface in order to provide ventilation. It comprises a source for respiratory gas, which is in the form of an electric motor with an impeller for example, and a device for determining pressure and/or flow and/or volume of the respiratory gas as well as a control unit (19) which is designed in such a manner that it determines a respiratory gas pressure for each breathing cycle on the basis of a predetermined value for the patient and/or on the basis of measurement signals for the pressure and/or flow and/or volume parameters and regulates the respiratory gas source in such a manner that the respiratory gas pressure is produced.

The control unit (19) is also designed in such a manner that it determines the instantaneous pressure and/or flow and/or volume of respiratory gas and displays the instantaneous value using the operating and information system (3) to the control unit. The control unit (19) is also designed in such a manner that it determines trend changes in its calculations over time based on one or more parameters, the trend changes being able to be displayed on the display.

The control unit (19) also compares those parameter values which have been specified by a user, for example upper and lower pressure limits or a maximum tolerable number of apnea per unit time or a maximum tolerable leakage, with the instantaneous values and generates an item of user information relating to deviations from the specification. The user information is preferably graphically visualized via the operating and information system (3).

Apnea and hypopnea are therefore identified from the measured respiratory flow by means of a decrease in the breathing (time) volume for a period of at least 10 s. Snoring is additionally identified via pressure and flow fluctuations, and flattening is identified via the inspiratory flow contour. Indices are calculated therefrom for each sufficiently long nighttime therapy, namely: AHI (=number of apnea+hypopnea for each artifact-free therapy duration), RDI (=number of all respiratory events for each artifact-free therapy duration), proportion of breaths with flattening, proportion of breaths with snoring. Data which allow deductions to be made about the usage behavior or the usage duration of the apparatus by the patient are preferably also determined. These data are determined and stored on a daily or weekly or monthly basis. If necessary, the usage data are retrieved and transmitted, possibly together with an apparatus identifier, via an Internet connection or a mobile radio connection.

Figure 2:
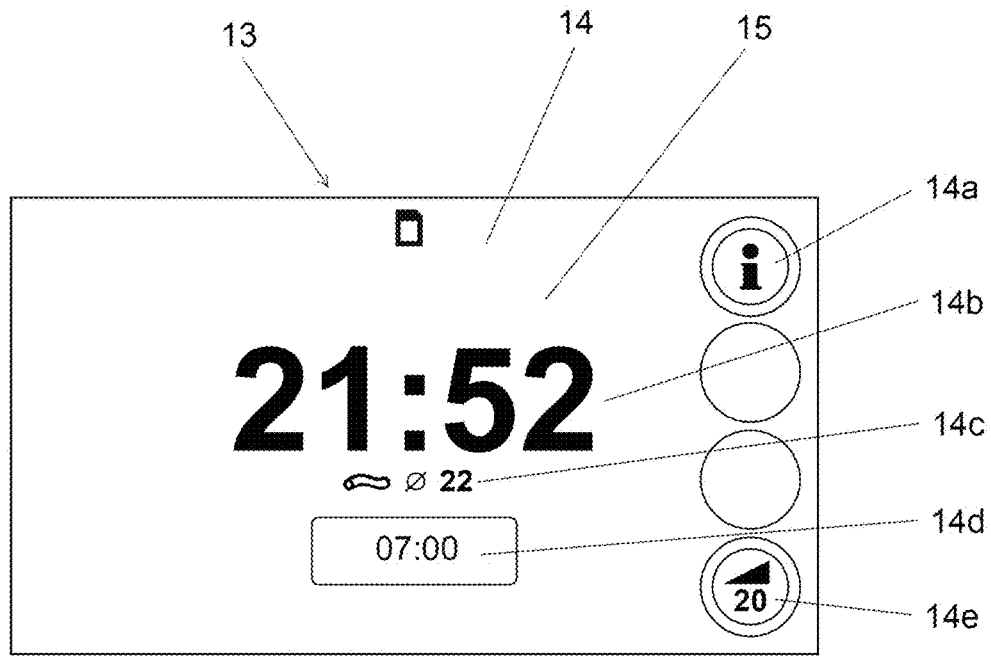
FIG. 2 shows a display of the operating and information system.
Figure 3:
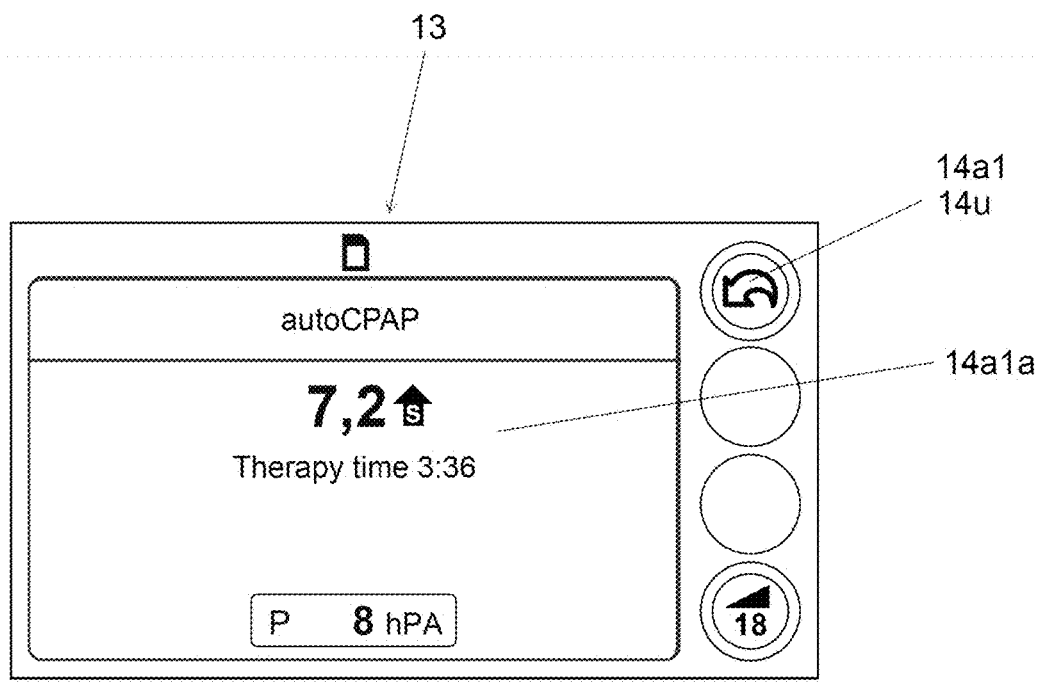
FIG. 3 shows a display for illustrating a submenu.

FIG. 2 shows the operating and information system (3) for a breathing apparatus (20) with a lit or backlit display (13) for displaying operating fields (14) or information for the user and with a touch-sensitive input unit (15) in spatial proximity to the displayed operating field (14). In a specific embodiment, it is a man-machine interface in the form of a so-called touchscreen, in which case a person skilled in the art knows different types which are all possible as part of the operating and information system (3) according to the invention.

At least one first operating field (14a) and one second operating field (14b) are displayed in the region of the display. The control unit (19) is configured to display the menu on the display (13).

A processing unit (18) which is coupled to the display (13) and to the touch-sensitive input unit (15) is configured to detect operation of the operating field (14) via the input unit (15) and, on the basis thereof, to control a function of the menu via the control unit (19). A menu assigned to an operating field (14b, 14c, 14d . . . ) is preferably displayed on the display (13) in a manner spatially adjacent to the operating field or at the same position of the operating field. Simultaneous or time-delayed operation of further operating fields (14b, 14c, 14d . . . ) via the input unit (15) can likewise be detected via the processing unit (18). The processing unit then causes the control unit (19) to call up the menu assigned to the selected operating field in the first level (=submenu). A submenu assigned to an operating field (14b, 14c, 14d . . . ) is preferably displayed on the display (13) in a manner spatially adjacent to the operating field or to the menu or at the same position of the operating field/menu.

A submenu is displayed by the control unit (19) via the display (13). The submenu is preferably displayed substantially at the same position as the menu from which the submenu emerges. Further operating fields (14) or information can now be displayed in the submenu. Navigation in a plurality of submenus is fundamentally provided; however, the branch is preferably no deeper than two menu levels. In order to return to the menu again from a submenu, an operating field (14) is always provided at the same position, the actuation of which field causes the control unit to display the menu of the next higher hierarchical level on the display (13).

The currently set ventilation pressure in mbar, with an associated operating field (14e), is displayed in the lower right-hand corner. An information field with an associated operating field (14a) is displayed in the upper right-hand corner.

If, for example, the ventilation pressure—as actuatable adjustment functions—is intended to be changed, the user simply touches the corresponding field of the display in which the information relating to the instantaneous pressure is displayed, here (14e). The control unit then causes an operating field (14e1) to be displayed.

In the simplest case, two operating fields in the form of + and − symbols (14f2, 14f3) are visualized above and below or to the right and left of the selected actuatable adjustment function. Actuation of the operating fields is detected by the processing unit (18) which then causes the control unit (19) to change the value of the actuatable adjustment functions in accordance with the input and to visualize it in the region of the display. The changed parameter is displayed by the control unit in the corresponding field of the display and is set and used as the new parameter at the same time or only after user selection by means of a control signal to the blower of the breathing apparatus. The set value and the actual value are preferably initially visualized and, after the actual value corresponds to the set value, only the actual value is displayed.

The parameters which have been adjusted in this manner are simultaneously written by the control unit (19) to a memory (21) which is used as a buffer for the parameter values to be currently used. The memory (21) always stores at least the values input and used last. If the undo function is actuated, the memory (21) always outputs these last values first.

Figure 4:
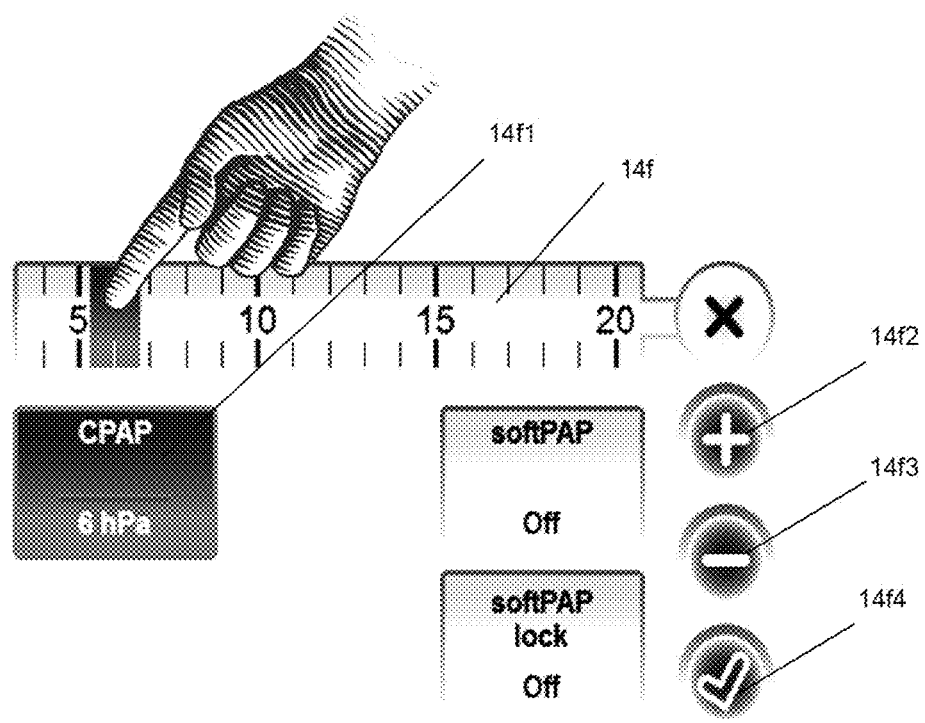
FIG. 4 shows an operating field in the form of a number line.

FIG. 4 shows an operating field in the form of a number line or bar. Parameters with a large number of adjustment levels, for example ventilation pressure, frequency, flow, volume or the background frequency (for example of 6-40 1/min) may be adjusted there.

In order to adjust a therapy pressure, the entire pressure range is preferably visualized on the display (13) in the form of a number line or bar. In addition, the visualized number line is also in the form of an operating field (14f). The operating field for the pressure (14f) is touch-sensitive over the entire visualized adjustment range. The user can therefore select the desired value by simply touching the desired pressure range. The detected value is visualized in an additional field (14/1). Provided that the detected and visualized value is correct, the user can use this value by touching the field (14/1). Fine adjustment with a step width of 0.5 is additionally possible using the symbols +/− (14/2, 14/3).

An operating field in the form of a list selection is displayed when adjusting a large number of options, for example for selecting the language for the user interface or for selecting the adjustment parameters for ventilation. In this case, the options which can be selected are displayed in written form or in the form of symbols and the desired option is selected by touching the latter, whereupon the control unit causes the selection to be implemented by means of a control signal or displays the adjustment range. In FIG. 5, the adjustments are discernible for the user at a glance. For adjustment, each value can be selected directly by touching.

An operating field can then be visualized in the form of a number line or bar, like in FIG. 4. There, parameters can be adjusted by touching the desired range.

The invention provides for an active operating field (14) to be highlighted by means of a more intensive color, as a result of which the user is made aware of the adjustment function, and operating fields which are not active are visualized in a faint color. The fainter color makes the user aware of the fact that the fields are not active.

Figure 5A:
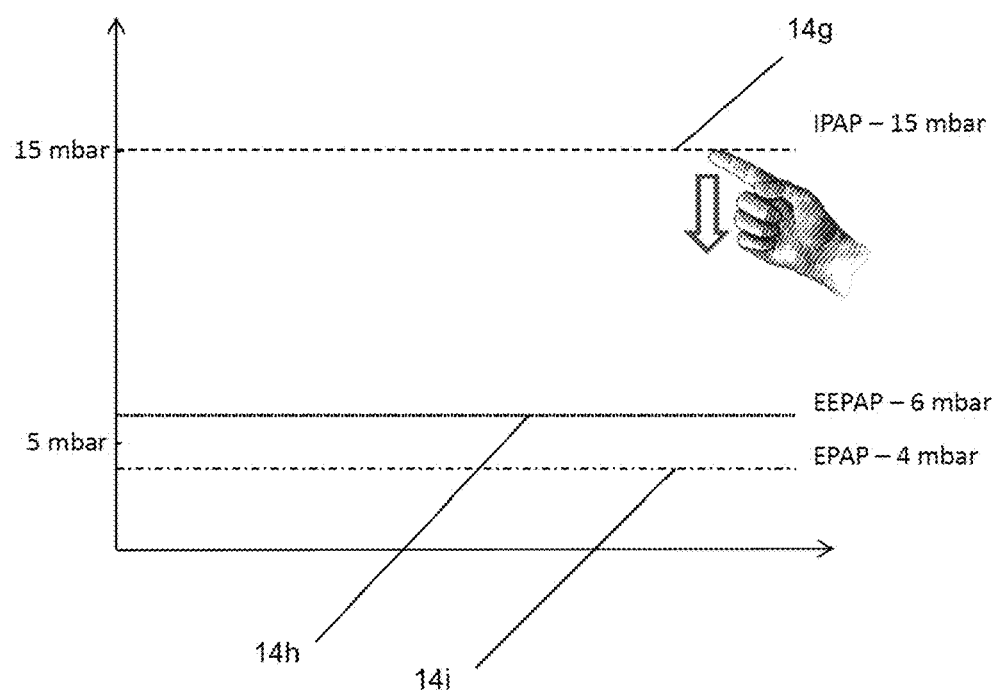
FIG. 5 shows an operating field in the form of a graph.

FIG. 5a shows an operating field in the form of a graph. Here, the instantaneous or stored pressure values for the inspiratory pressure (IPAP), the expiratory pressure (EPAP) and the end expiratory pressure level (EEPAP) are visualized.

Figure 5B:
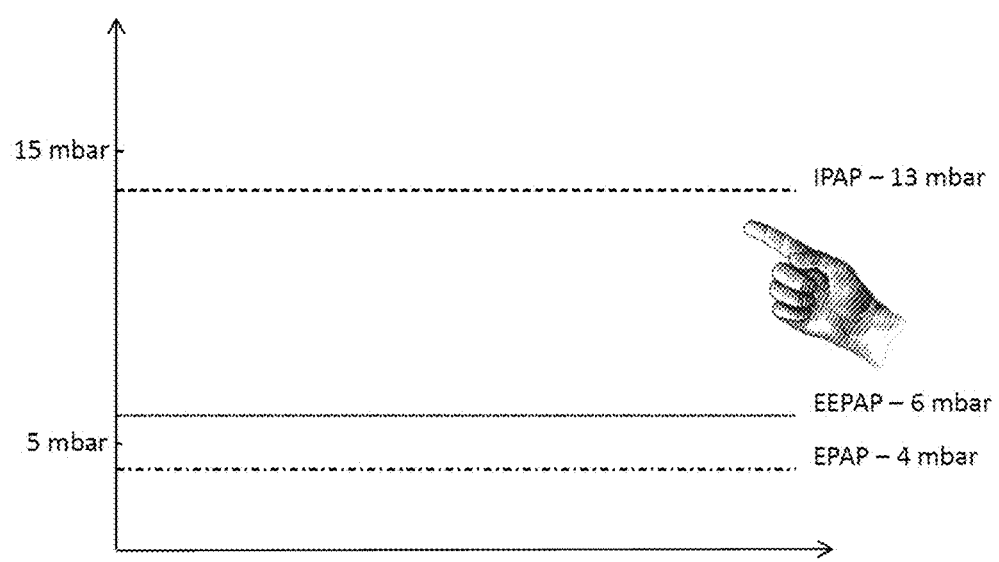

If the user wishes to change one of these pressures, he must touch the line representing the pressure range (14g, 14h, 14i) and must then move the pressure range to the desired level by sliding his finger across the display. In this case, the selected line moves with the movement and the value is also concomitantly displayed. If the user terminates the touching, this adjusted value is used. In the present example, the user has reduced the IPAP (14g) from 15 mbar to 13 mbar, as illustrated in FIG. 5b.

The user can likewise adjust the EPAP pressure (14i) and the EEPAP pressure (14h).

Figure 6A:
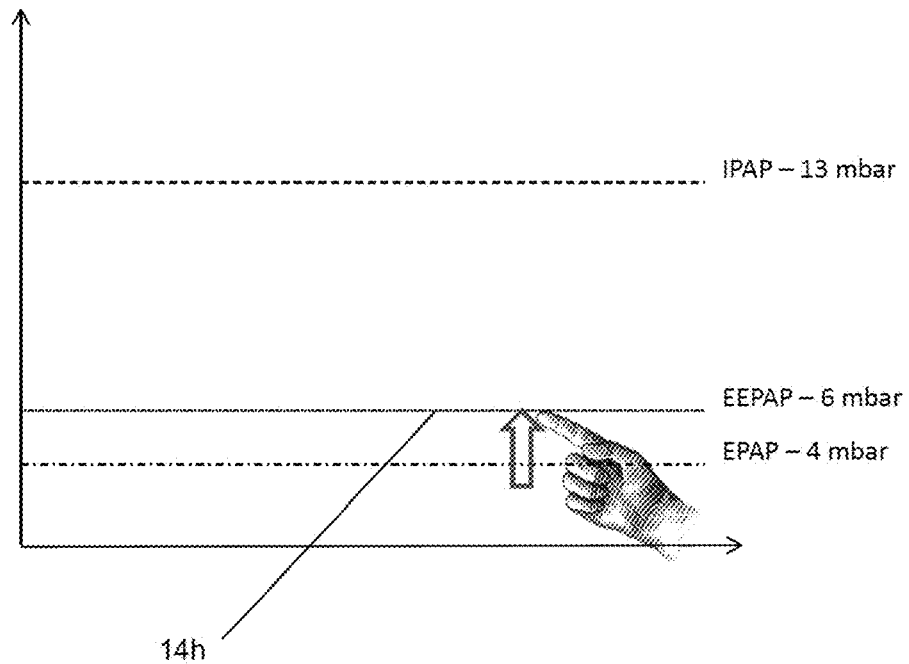
FIG. 6 shows an illustration similar to FIG. 5 for illustrating a further operating state, FIG. 7 a) shows a further operating field in the form of a graph, b) shows an adjustment of a pressure wave form, c) shows a variant of b)

FIG. 6a likewise shows an operating field in the form of a graph. Here, the instantaneous or stored pressure values for the inspiratory pressure (IPAP), the expiratory pressure (EPAP) and the end expiratory pressure level (EEPAP) are visualized.

Figure 6B:
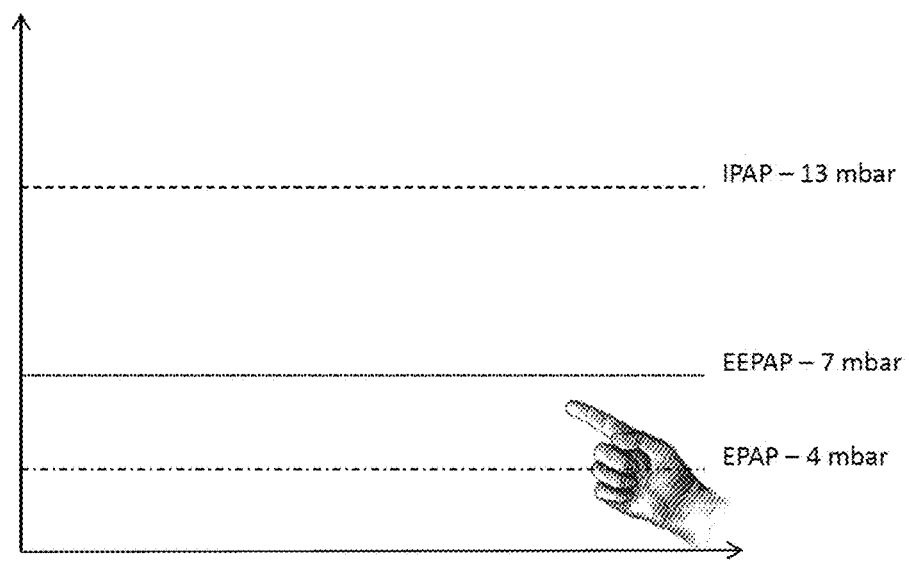

If the user wishes to change one of these pressures, he must touch the line representing the pressure range (14g, 14h, 14i) and must then move the pressure range to the desired level by sliding his finger across the display. In this case, the selected line moves with the movement and the value is also concomitantly displayed. If the user terminates the touching, this adjusted value is used. In the present example, the user has increased the EEPAP (14h) from 6 mbar to 7 mbar, as illustrated in FIG. 6b.

The user can likewise adjust the gradients of the pressure transitions and the pressure wave form.

Figure 7A:
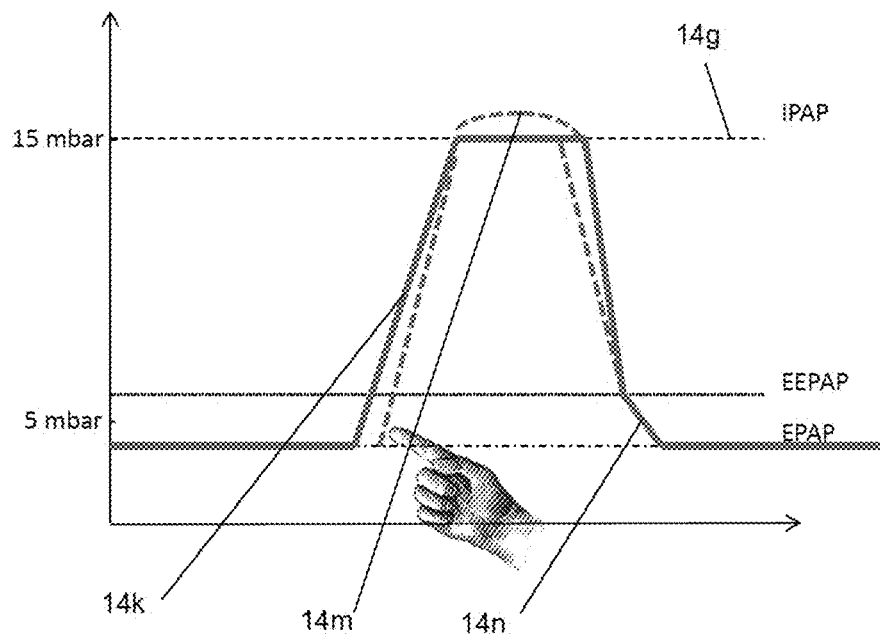

FIG. 7a shows an operating field in the form of a graph. Here, the instantaneous or stored pressure values for the inspiratory pressure (IPAP), the expiratory pressure (EPAP) and the end expiratory pressure level (EEPAP) are visualized. The gradients of the pressure transitions and the pressure wave form are also displayed. The gradient of the pressure transition from the EPAP to the IPAP pressure (14k) is sometimes displayed as a solid line (14k) and sometimes displayed as a dashed, interrupted line. The dashed, interrupted line appears when the user touches and moves the line (14k).

If the user wishes to change the gradient of the pressure transition from the EPAP to the IPAP pressure (14k), he must touch the line representing the gradient (14k) and then bring it to the desired gradient by shifting the line (14k)—preferably in the region of the start or end points, that is to say close to the EPAP or IPAP pressure—in the horizontal direction using his finger. In this case, the selected line (14k) concomitantly moves with the movement as an interrupted line, in which case the opposite anchor point of the line remains fixed. The selected line appears in dashed form, for example, or in another color during the adjustment process. In addition, the value of the gradient can be concomitantly displayed. If the user terminates the touching, this adjusted value is used and the line is solid again.

Figure 7B:
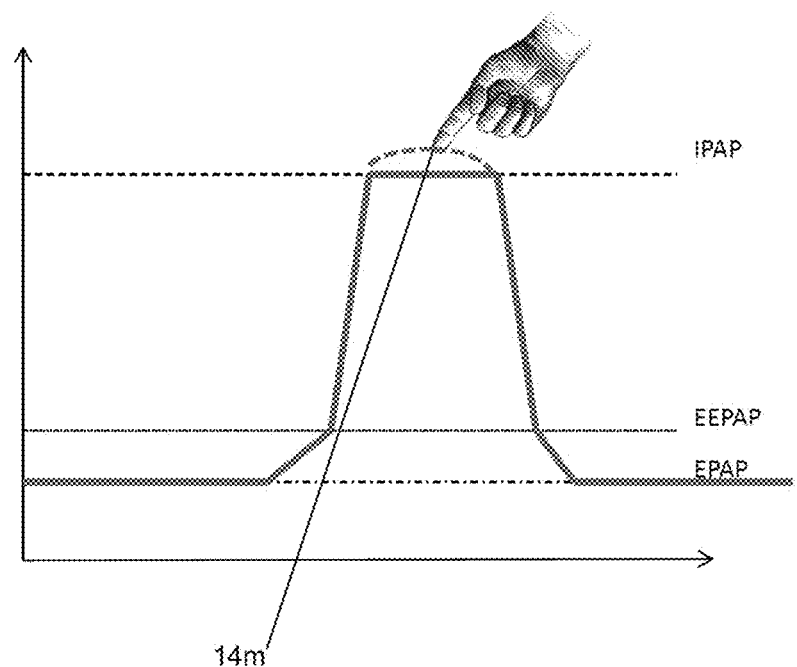

FIG. 7b shows how the pressure wave form (14m) is adjusted. The pressure wave form (14m) is an excessive increase in the IPAP pressure (14g) which can be adjusted by the user. The IPAP pressure is typically constant, here displayed as a solid line (14g). However, upon user selection, the IPAP pressure can be adjusted in a slightly rising manner to an increased IPAP pressure and in a slightly falling manner to the IPAP pressure, here displayed as an interrupted line.

Figure 7C:
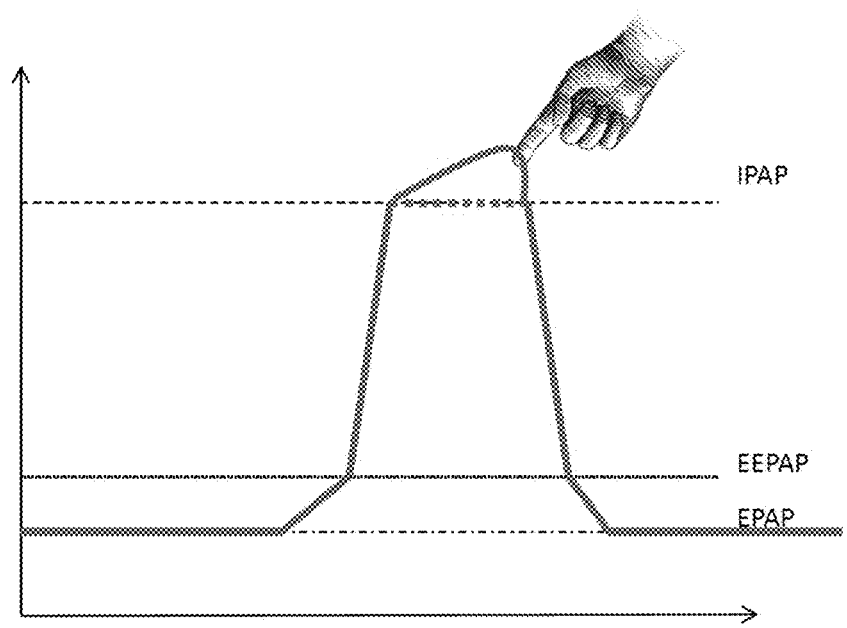

If the user wishes to change the pressure wave form (14m) of the IPAP pressure (14g), he must touch the line representing the IPAP (14g) and must then move it in the vertical direction in order to thus set the desired wave form. The maximum pressure of the wave form is always set in the region of the touching, and the rising and falling edges follow passively. If the user touches the line (14g) in the starting region (on the left) and moves it in the vertical direction, the resulting wave form (14m) will have a steep rise with a pressure maximum at the start and will then fall. If the user touches the line (14g) in the end region (on the right) and moves it in the vertical direction, the resulting wave form (14m) will have a gentle rise with a pressure maximum at the end and will then fall greatly (see FIG. 7c).

If the user touches the line (14g) in the center and moves it in the vertical direction, the resulting wave form (14m) will have a symmetrical rise and fall, with a pressure maximum in the center.

The following also applies to the statements made with respect to all Figures:

The displayed range of values on the number line is scaled in such a manner that it always includes precisely the range between the currently possible minimum and maximum for adjusting the respective parameter. In this case, possible presettings or limit values are taken into account.

Alternatively, a universal range of values is always displayed, and the currently valid (presettings or limit values) minimum and maximum are indicated, for example by means of additional lines or hatching of either the valid range of values or the invalid range of values.

The old value which is currently still active for ventilation until the new value is confirmed is additionally displayed. This can be effected, for example, by means of an additional line or a colored marking.

Instead of a line highlighted using color, the currently selected value can also be marked, for example, by means of an arrow which points to the scale from above or below, or by coloring a number on the scale.

Two or more values may also be simultaneously adjusted on a scale, for example the upper and lower pressure limits. In this case, both are displayed differently, for example by means of a different color or hatching. The changeover between the adjustment of the one value and the other value is carried out either within the scale, for example the parameter closest to the touching is always adjusted, or it is necessary to switch back and forth between the two parameters outside the scale, for example by means of activation using the tiles. Alternatively, the idea is also for a sensitive time window for adjusting the second value to remain after the first value has been adjusted, with the result that both values can be successively adjusted without diversions via menus on the displayed number line.

It is not always just numbers which must be present on the scale. It could also be possible to change over between different ranges which are described by words or by a combination of words and numbers, for example "small-medium-large-very large" or "off-slight-normal-strong", "off-0, 1, 2, . . . max".

While numerical values are adjusted on the number scale, there could be a further optical feedback region separate therefrom. For example, if the ramp gradient for the in-ex ramp is adjusted, a trapezium may be displayed at a further position on the display as a simplification of a pressure profile in which the ramp is displayed in a steeper or flatter manner similar to the selection in the operating field.

Acoustic feedback is also provided. For example, the greater the currently selected value in the operating field, the louder a tone or a tone sequence and vice versa. Alternatively, colored feedback is provided, for example a change in the color of the scale or the marking of the instantaneous value if the latter exceeds or undershoots particular values.

The following parameters can also be displayed using an operating field. Ramp gradients for the inspiration/expiration pressure transition and vice versa, trigger sensitivity, duration for the pressure ramp at the start of the therapy (soft start), volume of acoustic outputs, brightness of display or additional LEDs/display units, sensitivity of touchscreen or particular algorithm parts, target volume, target ventilation, patient characteristics such as height, age, weight, BMI or values related thereto, humidifier stage, desired values for at least one temperature or humidity of the respiratory gas, time, date, time zone, duration of a statistics period, size of an item of displayed information, target value for compliance in minutes or hours, at least one subjective mental state of a patient.

Instead of the linear display, the operating field may also be circular or oval and may therefore simulate a dial, for example.

The invention also provides for a virtual and rotatable control knob or a scrolling wheel to be displayed.

The number scale need not be linear and may also be logarithmic, for example, or may have a higher resolution, similar to a magnifying glass, in the range of the instantaneous value and may be coarser further away from it.

Alternatively, it is also possible to change over between a detailed display of a partial range, for example around the instantaneous value, and a display of the entire range.

In order to satisfy the respective patient, the rate of the pressure rise or flow rise may be stipulated. It is therefore stipulated how long the pressure rise lasts from the lower pressure level to the upper pressure level. In this case, the time is set in seconds or, for the flow, the gas flow is set in liters per minute. At the start of inspiration, the respiratory air is administered at a flow lower than the set flow, and the gas flow increases to the set value over the course of inspiration. These settings have immediate effects on the delivered tidal volume VT. The characteristics of the pressure increase or pressure reduction can be adjusted and are preferably effected in the form of a ramp. The pressure increase to the increased pressure level can take place with a uniform ramp gradient. The pressure increase or pressure reduction can be carried out with a variable ramp gradient. The value of the increased or reduced pressure level can preferably be adjusted in steps of mbar or fractions of mbar. The ramp gradient for the pressure rise or pressure drop can be displayed on the display at a further position in the form of a graph—for example a trapezium as a simplification of the pressure profile—in which the ramp is displayed in a steeper or flatter manner similar to the selection in the operating field.

Figure 8:
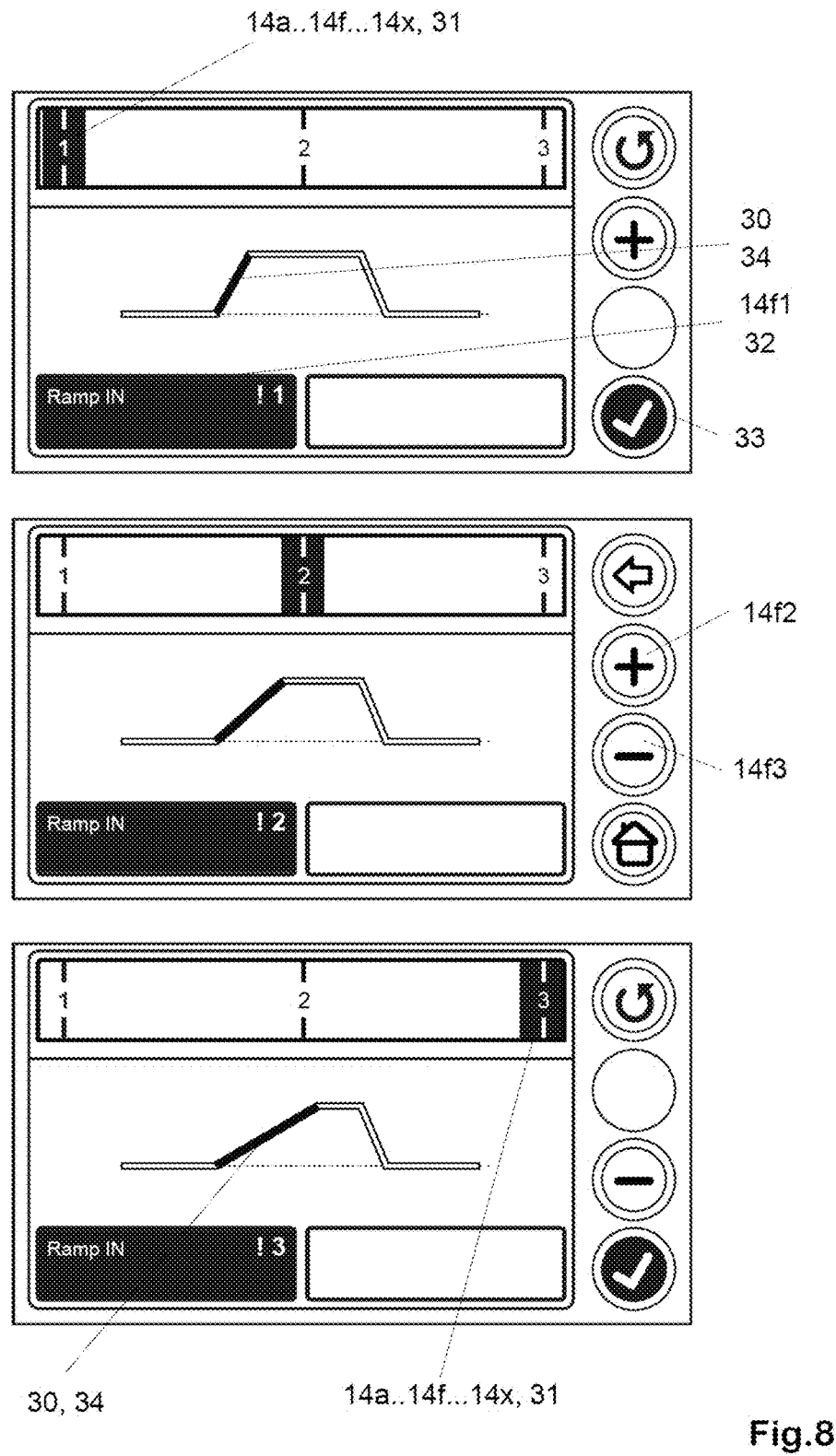
FIG. 8 shows a schematic illustration of a graphical adjustment aid for a ramp gradient.

FIG. 8 shows the graphical adjustment aid for the ramp gradient for the transition from expiratory pressure to inspiratory pressure (marked in green). The instantaneous level can be adjusted using a slider/ruler or alternatively with + and −. With its green marking, the ruler is additionally used not only as an adjustment tool but also as a display element. This provides the advantage that inexperienced users are also directly provided with a display of the value during adjustment.

In the example illustrated, it can be seen that the graphical adjustment aid provides the user with at least double feedback (31, 34), preferably triple feedback with respect to the adjustment (31, 32, 34). The operating device for a breathing apparatus comprises a touch-sensitive graphical display (3, 13, 14, 15) which at least occasionally represents the range of values for a breathing parameter (14a . . . 14x), here the ramp gradient (30), and numerically displays (31) at least individual values of the ramp gradient. In addition, a memory (21) for the value of the ramp gradient for at least one data point associated with the range of values and at least one position (14a . . . 14x) on the touch-sensitive graphical display which is associated with the data point using switching logic are used. Switching logic (18) which, when the position on the touch-sensitive graphical display which is associated with the data point using switching logic is touched, causes at least one numerical value (32) associated with the data point and/or a confirmation field (33) for the numerical value to be displayed and switching logic (18)

which, when the numerical value (32) or the confirmation field (33) is touched, applies this numerical value to the associated respiratory gas parameter and writes this numerical value, with the associated respiratory gas parameter, to the memory (21) are also provided.

The operating field is in the form of a number line or ruler and the entire range of values is visualized on the display (13) in the form of a number line or bar and the visualized number line is also in the form of an operating field (14*f*). The operating field is touch-sensitive over the entire visualized adjustment range and the desired value can be selected by only touching the desired range.

Finger pressure or touching inside the ruler is evaluated with respect to its position in such a manner that it is not necessary to strike precisely one of the numbers 1, 2, 3, but rather the finger pressure is assigned to the closest number. The detected value (32) is visualized in an additional field (14/1). The detected value can additionally be adjusted using the symbols +/− (14/2, 14/3).

Not only individual values of the ramp gradient are preferably numerically displayed (31), but the selected value of the ramp gradient is also numerically displayed (33) and the selected ramp gradient (34) is also graphically visualized.

Alternatively or additionally, as stated with respect to FIG. 7, the ramp can also be adjusted from the inspiratory to the expiratory pressure.

Figure 9:
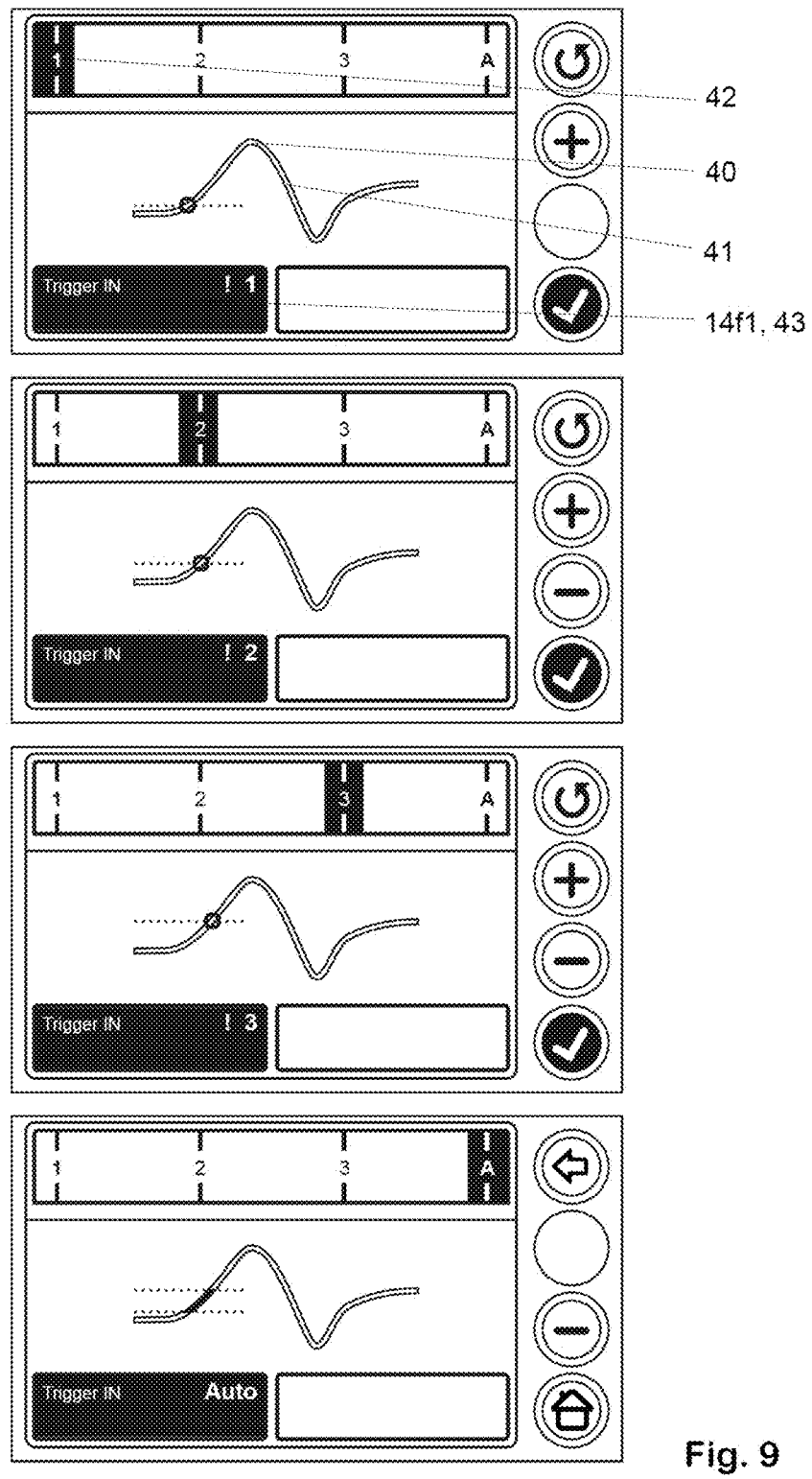
FIG. 9 shows a schematic illustration of a graphical adjustment aid for the trigger sensitivity.

In a similar manner to FIG. 8, FIG. 9 shows the adjustment of the trigger sensitivity (40). The threshold value (41) is schematically illustrated in the figure as a green line. In comparison with FIG. 7, it is seen that values which do not represent a numerical value can also be selected in the slider/ruler, in this case "A" for the auto level. The operating device for a breathing apparatus comprises a touch-sensitive graphical display (3, 13, 14, 15), which at least occasionally represents the range of values for a breathing parameter (14*a* . . . 14*x*), here the trigger sensitivity (40), and numerically displays (42) at least individual values of the trigger sensitivity, and a memory (21) for the value of the trigger sensitivity of at least one data point associated with the range of values. At least one position (14*a* . . . 14*x*) on the touch-sensitive graphical display which is associated with the data point using switching logic and switching logic (18) which, when the position on the touch-sensitive graphical display which is associated with the data point using switching logic is touched, causes at least one numerical value (32) associated with the data point and/or a confirmation field (33) for the numerical value to be displayed are likewise used. Switching logic (18) which, when the numerical value (32) or the confirmation field (33) is touched, applies this numerical value to the associated respiratory gas parameter and writes this numerical value, with the associated respiratory gas parameter, to the memory (21) is likewise provided.

The operating field is in the form of a number line or ruler and the entire range of values is visualized on the display (13) in the form of a number line or bar and the visualized number line is also in the form of an operating field (14*f*). The operating field is touch-sensitive over the entire visualized adjustment range and the desired value can be selected by only touching the desired range. Finger pressure or touching inside the ruler is evaluated with respect to its position in such a manner that it is not necessary to strike precisely one of the numbers 1, 2, 3, but rather the finger pressure is assigned to the closest number. The detected value (32) is visualized in an additional field (14/1).

The detected value can be additionally adjusted using the symbols +/− (14/2, 14/3). Not only individual values of the trigger sensitivity are preferably numerically displayed (42), but the selected value of the trigger sensitivity is also numerically displayed (43) and the selected trigger sensitivity is also graphically visualized (41).

Three fixed trigger levels are provided in the present case. However, they may also be adjusted using the symbols +/− (14/2, 14/3) in order to thus fine-tune the trigger on a patient-specific basis. If the level "A" is selected for the auto level, the trigger is adaptively adjusted within predefined limit values which are also graphically visualized.

Figure 10:
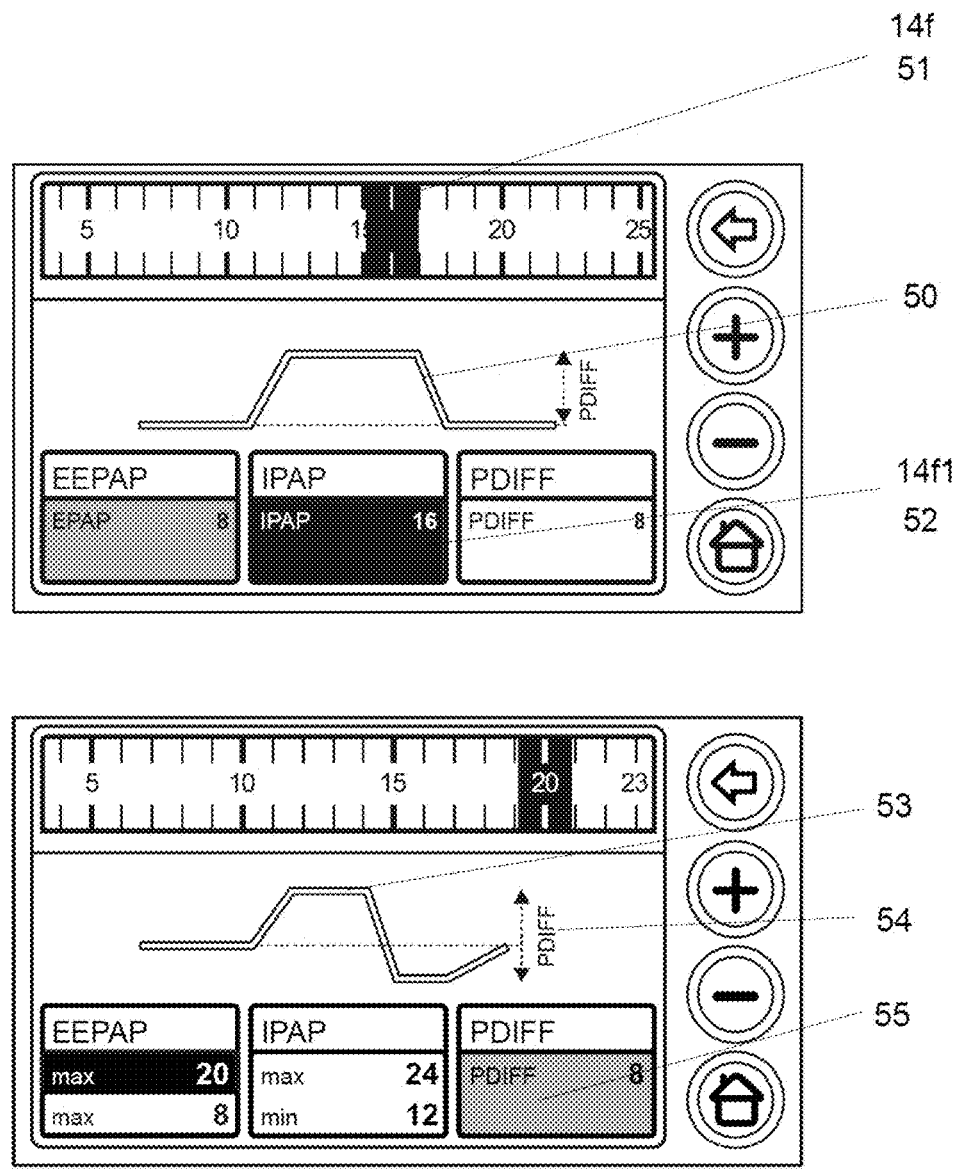
FIG. 10 shows a graphical adjustment aid for at least one pressure.

FIG. 10 shows the graphical adjustment aid for at least one inspiratory pressure and one expiratory pressure. The position of the pressure tile below the graph illustrates which is the inspiratory pressure and which is the expiratory pressure, and that PDIFF is the pressure swing (54). The color of the tiles represents:

green: currently selected parameter which can be adjusted using a slider or +/− keys gray: parameter which can alternatively be selected for adjustment black: informatively displayed parameter which is produced as a consequence of the adjustments.

Alternatively, not only the value of the parameter to be currently adjusted could be displayed in the slider in one color, but rather the values of further parameters could be additionally displayed using a marking which differs in terms of shape and/or color. The operating device for a breathing apparatus comprises a touch-sensitive graphical display (3, 13, 14, 15), which at least occasionally represents the range of values for a breathing parameter (14*a* . . . 14*x*), here the IPAP and/or EPAP and/or EEPAP pressure values (50), and numerically displays (51) at least individual values of the trigger sensitivity, a memory (21) for the pressure value, at least one data point associated with the range of values, at least one position (14*a* . . . 14*x*) on the touch-sensitive graphical display which is associated with the data point using switching logic, switching logic (18) which, when the position on the touch-sensitive graphical display which is associated with the data point using switching logic is touched, causes at least one numerical value (52) associated with the data point and/or a confirmation field for the numerical value to be displayed, and switching logic (18) which, when the numerical value (52) or the confirmation field is touched, applies this numerical value to the associated respiratory gas parameter and writes this numerical value, with the associated respiratory gas parameter, to the memory (21).

The operating field is in the form of a number line or ruler and the entire range of values is visualized on the display (13) in the form of a number line or bar and the visualized number line is also in the form of an operating field (14*f*). The operating field is touch-sensitive over the entire visualized adjustment range and the desired value can be selected by only touching the desired range. Finger pressure or touching within the ruler is evaluated with respect to its position in such a manner that it is not necessary to strike precisely one of the numbers, but rather the finger pressure is assigned to the closest number. The detected value (52) is visualized in an additional field (14/1), The detected value can be additionally adjusted using the symbols +/− (14/2, 14/3). Not only are individual pressure values preferably numerically displayed (52), but the selected value is also numerically displayed and the selected pressure is also graphically visualized (53). However, the latter can also be adjusted using the symbols +/− (14/2,

14/3). The resulting pressure swing is preferably also displayed as a numerical value (55) and graphically visualized (54) for information.

Figure 11:
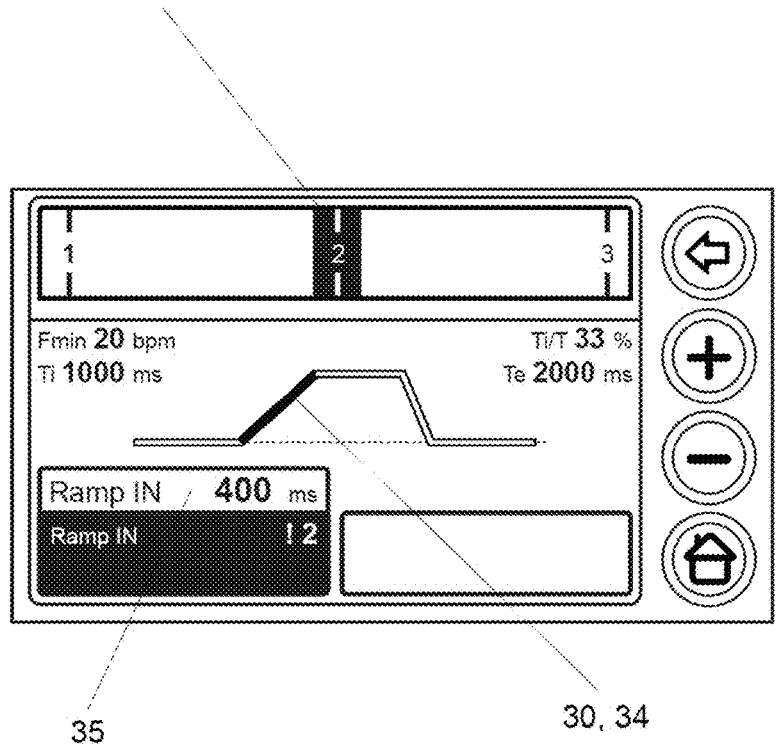
FIG. 11 shows an additional illustration for FIG. 7.

As an addition to FIG. 8 and in combination with the instantaneous ramp gradient 1, 2 or 3 (31), the adjustment of further parameters logically connected thereto is also informatively displayed according to FIG. 11. As a result, the user can usefully select the value to be currently adjusted without having to keep in mind all of the other parameters. As a consequence of the instantaneous ramp gradient and the other parameters, the currently valid ramp time in ms (35) is calculated and is likewise informatively displayed.

Figure 12:
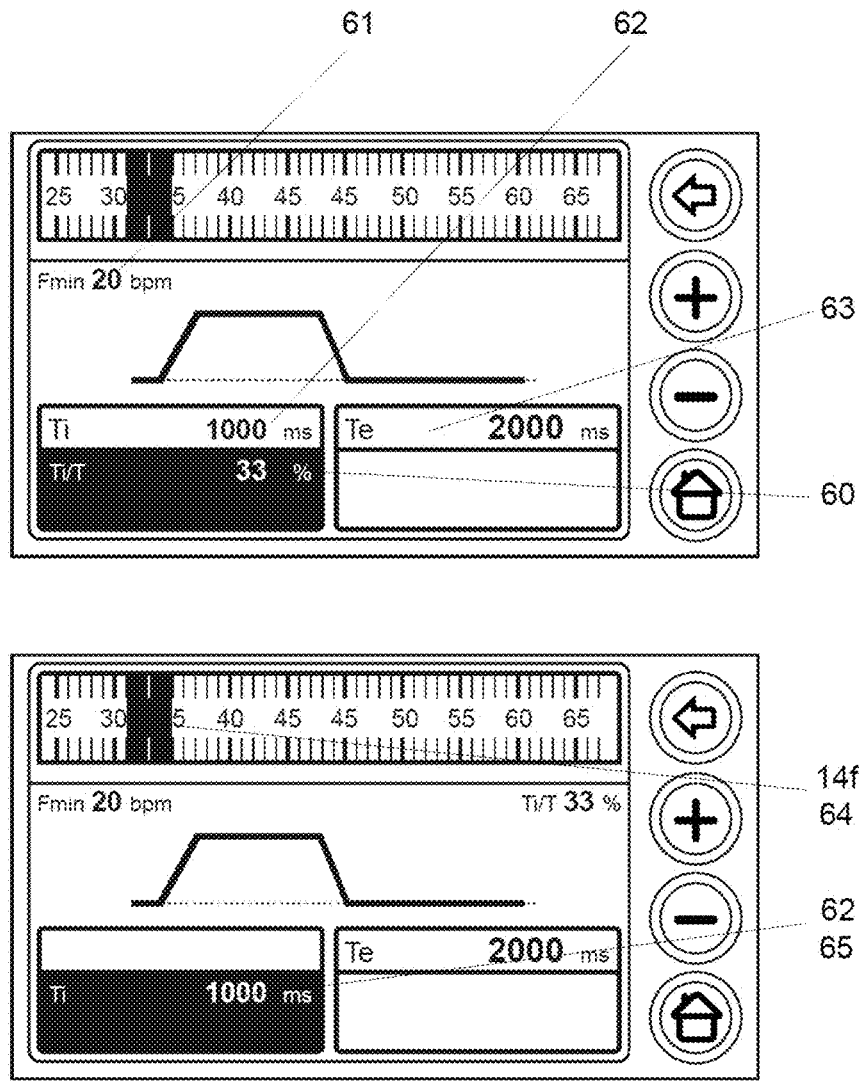
FIG. 12 shows an image for illustrating a ratio of inspiratory time and the total breathing time.

FIG. 12 shows the adjustment of the ratio of inspiratory time to the total breathing time in % (60). The selected breathing frequency (61) is additionally displayed. As a consequence of the adjusted breathing frequency and the adjusted ratio Ti/T, the inspiratory period Ti (62) and expiratory period Te (62) are calculated and informatively displayed.

The lower half illustrates an alternative embodiment in which the inspiratory period is adjusted, and the expiratory period and Ti/T automatically result therefrom in combination with the selected breathing frequency. The operating device for a breathing apparatus comprises a touch-sensitive graphical display (3, 13, 14, 15), which at least occasionally represents the range of values for a breathing parameter (14a . . . 14x), here the inspiration period (62), and numerically displays (64) at least individual values, a memory (21) for the inspiratory period, at least one data point associated with the range of values, at least one position (14a . . . 14x) on the touch-sensitive graphical display which is associated with the data point using switching logic, switching logic (18) which, when the position on the touch-sensitive graphical display which is associated with the data point using switching logic is touched, causes at least one numerical value (65) associated with the data point and/or a confirmation field for the numerical value to be displayed, and switching logic (18) which, when the numerical value (65) or the confirmation field is touched, applies this numerical value to the associated respiratory gas parameter and writes this numerical value, with the associated respiratory gas parameter, to the memory (21).

The operating field is in the form of a number line or ruler and the entire range of values is visualized on the display (13) in the form of a number line or bar and the visualized number line is also in the form of an operating field (14f). The operating field is touch-sensitive over the entire visualized adjustment range and the desired value can be selected by only touching the desired range.

Finger pressure or touching within the ruler is evaluated with respect to its position in such a manner that it is not necessary to strike precisely one of the numbers, but rather the finger pressure is assigned to the closest number. The detected value (52) is visualized in an additional field (14/1). The detected value can be additionally adjusted using the symbols +/− (14/2, 14/3). Not only are individual values preferably numerically displayed, but the selected value is also numerically displayed and the selected value is also graphically visualized. However, the latter can also be adjusted using the symbols +/− (14/2, 14/3). The resulting exhalation time (63) is preferably also displayed as a numerical value (63) and/or graphically visualized for information.

Figure 13:
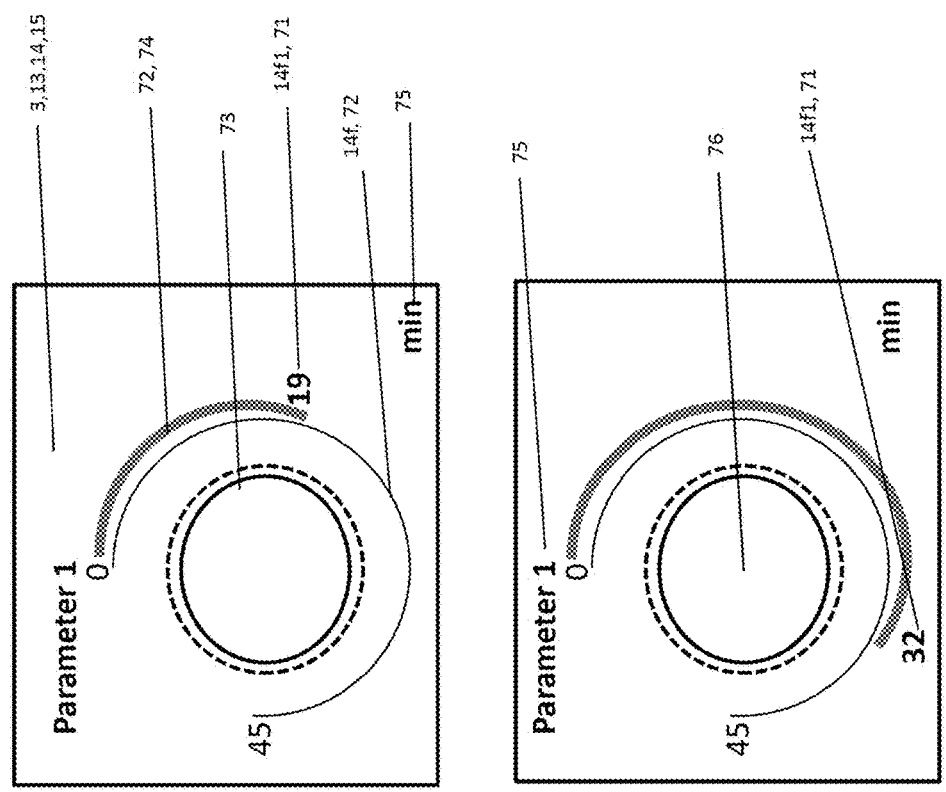
FIG. 13 shows a schematic illustration of a circular operating element.

FIG. 13 shows the described circular embodiment of the operating element. A dial which can be operated using a finger is simulated on a touch-sensitive display. A display element which is likewise circular and displays at least the currently set value—19 minutes in the example—particularly preferably also the value limits or the range of values—0 to 45 minutes in the example—is placed around the operating field. The display is effected as a number and additionally particularly preferably by means of a colored and/or thicker marking (74) which represents the instantaneous values in relation to the entire range of values.

The operating device for a breathing apparatus comprises a touch-sensitive graphical display (3, 13, 14, 15), which at least occasionally represents the range of values for a breathing parameter (14a . . . 14x) and numerically displays (71) at least individual values, a memory (21) for at least one data point associated with the range of values, at least one position (14a . . . 14x) on the touch-sensitive graphical display which is associated with the data point using switching logic, switching logic (18) which, when the position on the touch-sensitive graphical display which is associated with the data point using switching logic is touched, causes at least one numerical value (71) associated with the data point and/or a confirmation field for the numerical value to be displayed, and switching logic (18) which, when the numerical value (71) or the confirmation field is touched, applies this numerical value to the associated respiratory gas parameter and writes this numerical value, with the associated respiratory gas parameter, to the memory (21).

The operating field is in the form of a rotary knob or a dial (73) and the entire range of values or a partial range of values is visualized on the display (13) in the form of a numerical ring (72) and the visualized numerical ring is also in the form of an operating field (14f). The operating field is touch-sensitive over the entire visualized adjustment range and the desired value can be selected by only touching the desired range. Finger pressure or touching within the numerical ring is evaluated with respect to its position in such a manner that it is not necessary to strike precisely one of the numbers, but rather the finger pressure is assigned to the closest number.

Alternatively, swiping over the numerical ring is detected as an adjustment process and stopping of the swiping movement is detected as a selection. That value which is detected when the movement is stopped—the detected value (71)—is visualized in an additional field (14/1). The detected value can be additionally adjusted using the symbols +/− (14/2, 14/3). Not only are individual values preferably numerically displayed, but the selected value is also numerically displayed and the selected value is also graphically visualized. However, the latter can also be adjusted using the symbols +/− (14/2, 14/3).

The parameter (75) to be currently adjusted is particularly preferably displayed with its name and/or an internationally comprehensible symbol (75) and/or its unit (75). In the example illustrated, the parameter could be the ramp time as a sleeping aid of a therapy apparatus, which is displayed in minutes. Alternatively, therapy pressures or the power levels of a respiratory humidifier, inter alia, can be displayed and adjusted.

If the user carries out a rotational movement on the displayed dial using a finger, preferably in the clockwise direction, the selected value is increased, from 19 to 32 minutes in the example. A rotational movement in the opposite direction results in a reduction in the selected value. If the intended value is reached, it can be accepted and used by the apparatus. This is typically carried out either after expiry of a waiting time without further adjustment or after pressing a confirmation key/confirmation area (76) which is indicated, for example, with "accept", "ok", "use", a check symbol or the like. This is particularly preferably situated in the center of the displayed dial.

Figure 14:
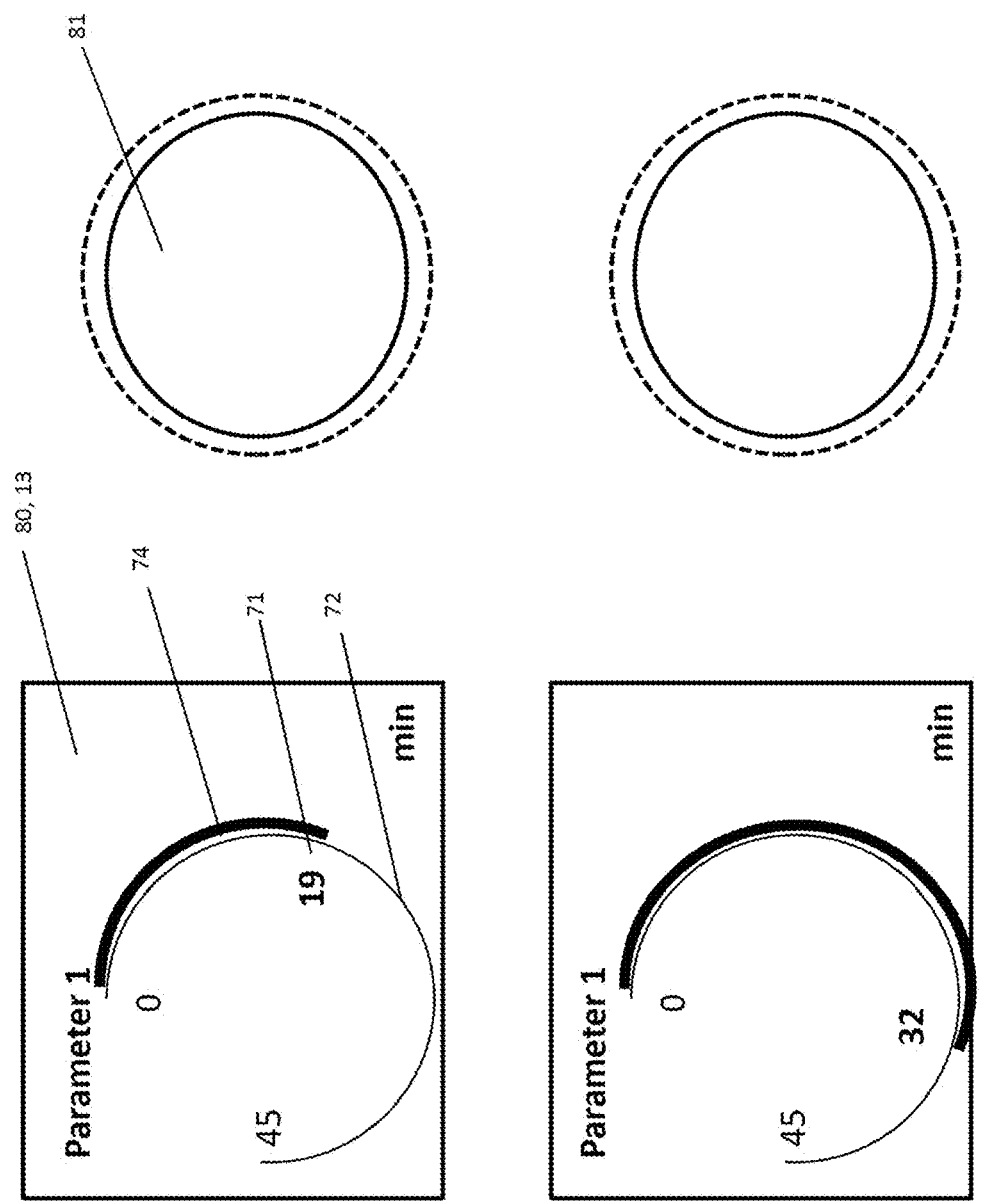
FIG. 14 shows an alternative embodiment.

FIG. 14 shows an alternative embodiment. In this case, the "dial" operating element and the circular display element are situated beside one another or below one another. This is a preferred embodiment if a touch-sensitive display element is not used, but rather only a graphical display element (80) having a separate mechanical rotary pushbutton (81). This embodiment provides an advantage since the mechanical rotary pushbutton (81) can preferably be used for fine adjustments owing to the haptics or better operability. The graphical visualization of the adjustment process and/or of the selected value and/or of the available range of values, which is decoupled from the mechanical rotary pushbutton (81), provides the advantage that a larger and improved display can be selected than could be provided by a scale beside the mechanical rotary pushbutton (81).

In this case, a selected value is particularly preferably confirmed by pressing the rotary pushbutton (81).

Otherwise, the type of display and adjustment is comparable with the exemplary embodiment in FIG. 13, which is why the description with respect to FIG. 13 can also be used for the example in FIG. 14.

Figure 15:
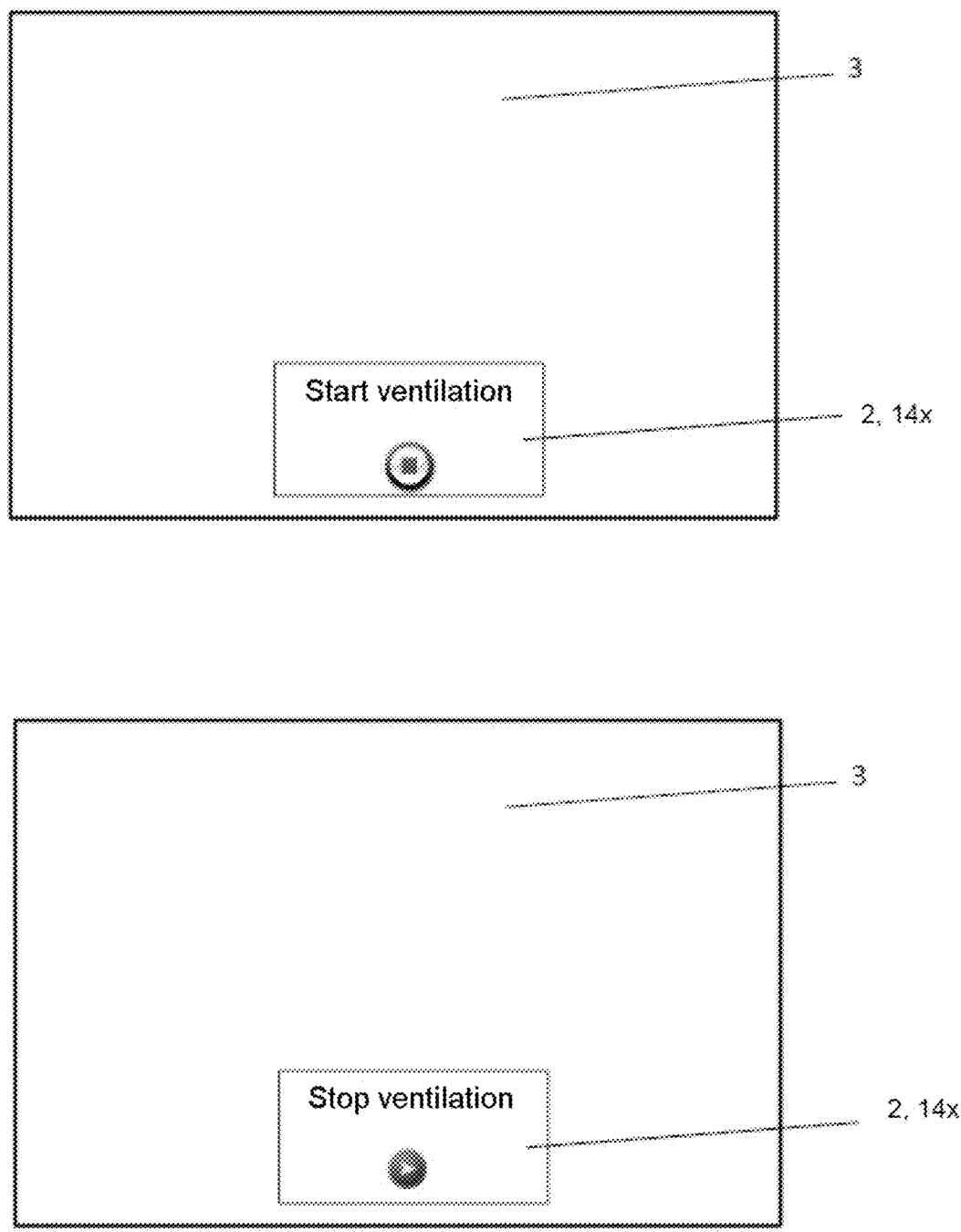
FIG. 15 shows a mechanical operating element.

According to the invention, a (start/stop) operating area (14x) can be provided on the touchscreen or a mechanical (start/stop) operating element (2) according to FIG. 15 can be provided, the actuation of which causes the operating and information system (3) to start or stop the ventilation via the control unit.

The invention provides for the (start/stop) operating area (14x) on the touchscreen to have a different form depending on the situation; for example, if the ventilation is not active but can be started, the (start/stop) operating area (14x) on the touchscreen at least partially has a green color, for example, or has a start symbol and additionally has an item of written information "start ventilation", for example. If the ventilation is active and can be stopped, the (start/stop) operating area (14x) on the touchscreen at least partially has a red color or has a stop symbol and additionally has an item of written information "stop ventilation", for example.

In this case, provision is made, for example, for the (start/stop) operating area (14x) to otherwise appear unchanged always at the same position on the touchscreen and/or always in the same size.

If the (start/stop) operating area (14x) on the touchscreen for stopping the ventilation "stop ventilation" is confirmed, instantaneous settings for the ventilation, for example instantaneous pressure values, are stored by the control unit in a retrievable manner and are read out again in response to actuation of the (start/stop) operating area (14x) again—for starting the ventilation—and are activated for the ventilation, in particular provided that no changes were made to the ventilation settings while ventilation was stopped.

What is claimed is:

1. An operating device for a breathing apparatus, wherein the device comprises a touch-sensitive graphical display which at least occasionally represents a range of values for a ventilation parameter and numerically displays at least individual values, and a memory for ventilation parameter values, and further comprises
at least one data point associated with the range of values,
at least one position on the touch-sensitive graphical display which is associated with the data point using switching logic,
a switching logic which, when the position on the touch-sensitive graphical display which is associated with the data point using switching logic is touched, causes at least one numerical value associated with the data point and/or a confirmation field for a numerical value to be displayed,
a switching logic which, when the numerical value or the confirmation field is touched, applies this numerical value to an associated respiratory gas parameter and writes this numerical value, together with the associated respiratory gas parameter, to the memory.

2. The device of claim 1, wherein the ventilation parameter is the pressure or flow or volume or frequency or IPAP or EPAP or PEEP or FiO2.

3. The device of claim 1, wherein the operating field is in the form of a number line or bar and an entire range of values is visualized on the display in the form of a number line or bar, the visualized number line being also in the form of an operating field.

4. The device of claim 1, wherein the operating field is touch-sensitive over an entire visualized adjustment range.

5. The device of claim 1, wherein a desired value can be selected by merely touching a desired range.

6. The device of claim 1, wherein a detected value is visualized in an additional field.

7. The device of claim 6, wherein the detected value is additionally available for fine adjustment using the symbols +/−.

8. The device of claim 1, wherein the memory stores at least a value used and input last and a value used and input chronologically before said value and the memory always outputs the chronologically most recent value first if an undo function is actuated.

9. The device of claim 1, wherein at least one collection of ventilation parameters stored in the memory in a retrievable manner comprises at least three preset parameters selected from pressure or flow or volume or frequency or IPAP or EPAP or PEEP or FiO2, and a region in which a collection of ventilation parameters is graphically represented is provided for this collection of ventilation parameters in a region of the touch-sensitive graphical display, and the device further comprises
at least one data point associated with the collection of ventilation parameters,
at least one position on the touch-sensitive graphical display which is associated with the data point using switching logic,
switching logic which, when the position on the touch-sensitive graphical display which is associated with the data point using switching logic is touched, causes at least one collection of ventilation parameters associated with the data point and/or a confirmation field for the collection of ventilation parameters to be displayed,
a switching logic which, when the numerical value or the collection of ventilation parameters is touched, uses this collection of ventilation parameters.

10. The device of claim 1, wherein the device further comprises a graphical adjustment aid for at least one ramp gradient.

11. The device of claim 1, wherein the device further comprises a graphical adjustment aid for trigger sensitivity is provided.

12. The device of claim 1, wherein at least one adjustment element is in the form of a dial.

13. The device of claim 1, wherein at least one circular display element is present.

14. The device of claim 1, wherein a rotary pushbutton is present.

15. The device of claim 1, wherein a start/stop area is present.

16. The device of claim 15, wherein the start/stop operating area is arranged in a region of the touchscreen and/or can be generated in different forms by an apparatus controller.

17. The device of claim 1, wherein individual values of a ventilation parameter are numerically displayed and a selected value is also numerically displayed and the selected ventilation parameter is graphically visualized.

18. The device of claim 1, wherein three fixed levels are provided for the ventilation parameter and these levels can be adjusted using the symbols +/− to thereby fine-tune the ventilation parameter on a patient-specific basis.

19. The device of claim 1, wherein the device comprises a graphical display element instead of a touch-sensitive display element and the graphical display element comprises a separate mechanical operating element, adjustments made using the mechanical operating element being graphically visualized on the graphical display element.

20. The device of claim 19, wherein a change in values during an adjustment process using the mechanical operating element and/or a selected value and/or an available range of values is visualized on the graphical display element.

21. An operating device for a breathing apparatus, wherein the device comprises:
   (a) a graphical display which at least occasionally represents a range of values for a ventilation parameter and numerically displays at least individual values, and a memory for breathing parameter values,
and further comprises
   (b) at least one data point associated with the range of values, at least one position on the graphical display which is associated with the data point using switching logic,
   (c) a switching logic which, when a position of a mechanical operating element assigned to the data point using switching logic is actuated,
   (d) causes at least one numerical value assigned to the data point and/or a confirmation field for the numerical value to be displayed,
   (e) a switching logic which, when the position of the mechanical operating element assigned to the data point using switching logic is actuated, applies this numerical value to an associated respiratory gas parameter and writes this numerical value, together with the associated respiratory gas parameter, to the memory.

* * * * *